United States Patent
Aoyama

(10) Patent No.: US 10,132,761 B2
(45) Date of Patent: Nov. 20, 2018

(54) METHOD OF CONSTRUCTING 3D IMAGE, IMAGE PROCESSOR, AND ELECTRON MICROSCOPE

(71) Applicant: JEOL Ltd., Tokyo (JP)

(72) Inventor: Yoshitaka Aoyama, Tokyo (JP)

(73) Assignee: JEOL Ltd., Tokyo (JP)

(*) Notice: Subject to any disclaimer, the term of this patent is extended or adjusted under 35 U.S.C. 154(b) by 411 days.

(21) Appl. No.: 14/836,024

(22) Filed: Aug. 26, 2015

(65) Prior Publication Data

US 2016/0079031 A1 Mar. 17, 2016

(30) Foreign Application Priority Data

Aug. 29, 2014 (JP) .................... 2014-175640

(51) Int. Cl.
*H01J 37/22* (2006.01)
*G01N 23/046* (2018.01)
*G01N 23/2252* (2018.01)

(52) U.S. Cl.
CPC ....... *G01N 23/046* (2013.01); *G01N 23/2252* (2013.01); *H01J 37/22* (2013.01); *H01J 2237/226* (2013.01); *H01J 2237/2611* (2013.01); *H01J 2237/2807* (2013.01)

(58) Field of Classification Search
CPC .................................................. H01J 37/222
See application file for complete search history.

(56) References Cited

U.S. PATENT DOCUMENTS

| | | | | |
|---|---|---|---|---|
| 2008/0296498 | A1* | 12/2008 | Hong | H01J 37/3056 250/311 |
| 2013/0234024 | A1* | 9/2013 | Kubo | H01J 37/222 250/307 |
| 2013/0248354 | A1* | 9/2013 | Keady | H01J 37/3005 204/192.33 |
| 2016/0027612 | A1* | 1/2016 | Fischione | H01J 37/20 250/307 |

FOREIGN PATENT DOCUMENTS

JP 2012209050 A 10/2012

* cited by examiner

*Primary Examiner* — Tung Vo
*Assistant Examiner* — Rowina Cattungal
(74) *Attorney, Agent, or Firm* — The Webb Law Firm

(57) ABSTRACT

A method capable of constructing an accurate three-dimensional image is offered. The method comprises the step (S10) of obtaining a first series of tilted images which are constituted by electron microscope images or elemental mapping images of a sample (S) at different tilt angles and which have been obtained by tilting the sample in angular increments, the step (S14) of obtaining a second series of tilted images which are constituted by electron microscope images or elemental mapping images of the sample at different tilt angles and which have been obtained by rotating the sample about an axis (P) perpendicular to a surface (Sf) of the sample and then tilting the sample in angular increments, and the step (S16) of constructing the three-dimensional image on the basis of the first and second series of tilted images.

7 Claims, 10 Drawing Sheets

METHOD OF CONSTRUCTING 3D IMAGE, IMAGE PROCESSOR, AND ELECTRON MICROSCOPE

BACKGROUND OF THE INVENTION

Field of the Invention

The present invention relates to a method of constructing a three-dimensional (3D) image, image processor, and electron microscope.

Description of Related Art

Electron tomography (ET) has been known as a technique for observing and analyzing the morphology of a sample in a three-dimensional manner by applying a computerized tomography (CT) method to an electron microscope such as a transmission electron microscope (TEM) or a scanning transmission electron microscope (STEM) (see, for example, JP-A-2012-209050).

In recent years, EDS tomography that is a combination of energy dispersive X-ray spectroscopy (EDS) and electron tomography (ET) has attracted attention. EDS tomography is a method of three-dimensional elemental analysis in which EDS and ET are combined.

A process of EDS tomography starts with acquiring elemental mapping images by tilting a sample at various angles using an electron microscope. For example, the angular range of tilt is set to ±60 degrees, and the sample is tilted in increments of 5 degrees. If an elemental mapping image is acquired at each tilt angle, then a series of tilted images consisting of 25 elemental mapping images can be obtained. Then, computer tomography is applied to the elemental mapping images constituting the series of tilted images, thus obtaining two-dimensional reconstructed cross-sectional images. A three-dimensional image showing a three-dimensional elemental distribution is derived by superimposing the resulting, series of cross-sectional images.

Generally, when a sample is to be observed in an electron microscope, the sample is held on a mesh having a diameter of 3 mm. If the sample is tilted in increments in an attempt to obtain a series of tilted images, the EDS detector is hidden in a shadow of the frame of the sample holder, mesh, or sample at a certain tilt angle. Consequently, characteristic X-rays produced from the sample are cut off, decreasing the X-ray intensity. Also, the brightness levels of elemental mapping images decrease. These present the problem that the accuracy of three-dimensional images will deteriorate.

SUMMARY OF THE INVENTION

In view of the foregoing problem, the present invention has been made. One object associated with some aspects of the present invention is to provide a method and image processor capable of constructing an accurate three-dimensional image. Another object associated with some aspects of the present invention is to provide an electron microscope including this image processor.

(1) A method associated with the present invention to construct a three-dimensional image starts with obtaining a first series of tilted images which are constituted by electron microscope images or elemental mapping images of a sample at different tilt angles and which have been obtained by tilting the sample in a plurality of angular increments. Then, a second series of tilted images which are constituted by electron microscope images or elemental mapping images of the sample at different tilt angles are obtained. The second series of tilted images has been obtained by rotating the sample about an axis perpendicular to a surface of the sample and then tilting the sample in a plurality of angular increments. The three-dimensional image is constructed on the basis of the first and second series of tilted images.

In this method of constructing a three-dimensional image, the three-dimensional image is constructed on the basis of the first and second series of tilted images. Therefore, a three-dimensional image can be constructed by replacing electron microscope images or elemental mapping images which are included in the electron microscope images or elemental mapping images constituting the first series of tilted images and which have deteriorated in brightness level because signals arising from the sample such as secondary electrons and characteristic X-rays were cut off by a sample holder and so on by the electron microscope images or elemental mapping images constituting the corresponding second series of tilted images. This can reduce the dependence of the elemental mapping images forming the series of tilted images for constructing a three-dimensional image on tilt angle. Consequently, an accurate three-dimensional image can be derived.

(2) In one feature of this method of constructing a three-dimensional image, there may be further provided the step of rotating the sample through 180 degrees about an axis perpendicular to the surface of the sample after the step of obtaining the first series of tilted images and prior to the step of obtaining the second series of tilted images.

In this method of constructing a three-dimensional image, the electron microscope images or elemental mapping images constituting the second series of tilted images can be made to correspond to the electron microscope images or elemental mapping images constituting the first series of tilted images by rotating the electron microscope images or elemental mapping images constituting the second series of tilted images through 180 degrees. In consequence, the electron microscope images or elemental mapping images constituting the first series of tilted images can be easily replaced by the electron microscope images or elemental mapping images constituting the second series of tilted images.

(3) In another feature of this method of constructing a three-dimensional image, during the step of constructing the three-dimensional image, the second series of tilted images may be rotated to the same orientation as the first series of tilted images. Some of the electron microscope images or elemental mapping images of the sample constituting the first series of tilted images may be replaced by some of the electron microscope images or elemental mapping images of the sample constituting the second series of tilted images so as to create a third series of tilted images, thus constructing the three-dimensional image.

In this method of constructing a three-dimensional image, the dependence of the elemental mapping images constituting the third series of tilted images on tilt angle can be reduced. As a consequence, an accurate three-dimensional image can be derived.

(4) Another method associated with the present invention to construct a three-dimensional image starts with obtaining a first series of tilted images which are constituted by electron microscope images or elemental mapping images of a sample at different tilt angles and which have been obtained by tilting the sample in a plurality of angular increments. Then, a second series of tilted images which are constituted by electron microscope images or elemental mapping images of the sample at different tilt angles and which have been obtained by turning the sample upside down and then tilting the sample in a plurality of angular increments is obtained. The three-dimensional image is constructed on the basis of the first and second series of tilted images.

In this method of constructing a three-dimensional image, the three-dimensional image is constructed on the basis of the first and second series of tilted images. Therefore, a three-dimensional image can be formed by replacing electron microscope images or elemental mapping images which are included in the electron microscope images or elemental mapping images constituting the first series of tilted images and which have deteriorated in brightness level because signals arising from the sample were cut off by a sample holder and so on by the electron microscope images or elemental mapping images constituting the corresponding second series of tilted images. This can reduce the dependence of the elemental mapping images forming the series of tilted images for constructing a three-dimensional image on tilt angle. Consequently, an accurate three-dimensional image can be derived.

(5) In one feature of this method of constructing a three-dimensional image, there may be further provided the step of turning the sample upside down after the step of obtaining the first series of tilted images and prior to the step of obtaining the second series of tilted images.

(6) In another feature of this method of constructing a three-dimensional image, the three-dimensional image may be constructed by reversing the second series of tilted images to the same orientation as the first series of tilted images and replacing some of the electron microscope images or elemental mapping images of the sample constituting the first series of tilted images by some of the electron microscope images or elemental mapping images of the sample constituting the second series of tilted images so as to create a third series of tilted images.

In this method of constructing a three-dimensional image, the dependence of the elemental mapping images forming the third series of tilted images on tilt angle can be reduced. Consequently, an accurate three-dimensional image can be derived.

(7) In one feature of any one of these methods of constructing a three-dimensional image, the elemental mapping images of the sample may be obtained by irradiating the sample with an electron beam to induce X-rays and detecting the X-rays by an energy dispersive X-ray detector.

In this method of constructing a three-dimensional image, an accurate three-dimensional elemental distribution image can be obtained.

(8) An image processor associated with the present invention comprises: a first series tilted image acquisition portion for obtaining a first series of tilted images which are constituted by electron microscope images or elemental mapping images of a sample at different tilt angles and which have been obtained by tilting the sample in a plurality of angular increments; a second series tilted image acquisition portion for obtaining a second series of tilted images which are constituted by electron microscope images or elemental mapping images of the sample at different tilt angles and which have been obtained by rotating the sample about an axis perpendicular to a surface of the sample and then tilting the sample in a plurality of angular increments; and a three-dimensional image constructing portion for constructing a three-dimensional image on the basis of the first and second series of tilted images.

In this image processor, a three-dimensional image is constructed on the basis of the first and second series of tilted images and, therefore, a three-dimensional image can be constructed by replacing electron microscope images or elemental mapping images which are included in the electron microscope images or elemental mapping images constituting the first series of tilted images and which have deteriorated in brightness level because signals emanating from the sample were cut off by a sample holder and so on by the electron microscope images or elemental mapping images constituting the corresponding second series of tilted images. Consequently, the dependence of the elemental mapping images constituting the series of tilted images for constructing a three-dimensional image on tilt angle can be reduced. Hence, an accurate three-dimensional image can be obtained.

(9) In one feature of this image processor, the second series of tilted images may be constituted by electron microscope images or elemental mapping images of the sample obtained after rotating the sample about an axis perpendicular to the surface of the sample through 180 degrees when the sample is in the same state as when the first series of tilted images was obtained.

In this image processor, the electron microscope images or elemental mapping images constituting the second series of tilted images can be made to correspond to the electron microscope images or elemental mapping images constituting the first series of tilted images by rotating the electron microscope images or elemental mapping images constituting the second series of tilted images through 180 degrees. Consequently, the electron microscope images or elemental mapping images constituting the first series of tilted images can be easily replaced by the electron microscope images or elemental mapping images constituting the second series of tilted images.

(10) In another feature of this image processor, the three-dimensional image constructing portion may construct the three-dimensional image by rotating the second series of tilted images to the same orientation as the first series of tilted images and replacing some of the electron microscope images or elemental mapping images of the sample constituting the first series of tilted images by some of the electron microscope images or elemental mapping images of the sample constituting the second series of tilted images so as to create a third series of tilted images.

This image processor permits the dependence of the elemental mapping images constituting the third series of tilted images on tilt angle to be reduced and so an accurate three-dimensional image can be obtained.

(11) Another image processor associated with the present invention comprises: a first series tilted image acquisition portion for obtaining a first series of tilted images which are constituted by electron microscope images or elemental mapping images of a sample at different tilt angles and which have been obtained by tilting the sample in a plurality of angular increments; a second series tilted image acquisition portion for obtaining a second series of tilted images which are constituted by electron microscope images or elemental mapping images of the sample at different tilt angles and which have been obtained by turning the sample upside down and then tilting the sample in a plurality of angular increments; and a three-dimensional image constructing portion for constructing a three-dimensional image on the basis of the first and second series of tilted images.

In this image processor, a three-dimensional image is constructed on the basis of the first and second series of tilted images and so a three-dimensional image can be fabricated by replacing electron microscope images or elemental mapping images which are included in the electron microscope images or elemental mapping images constituting the first series of tilted images and which have deteriorated in brightness level because signals emanating from the sample were cut off by a sample holder and so on by the electron microscope images or elemental mapping images constituting the corresponding second series of tilted images. Consequently, the dependence of the elemental mapping images constituting the series of tilted images for constructing a three-dimensional image on tilt angle can be reduced. As a result, an accurate three-dimensional image can be derived.

(12) In one feature of this image processor, the three-dimensional image constructing portion may construct the three-dimensional image by reversing the second series of tilted images to the same orientation as the first series of tilted images and replacing some of the electron microscope images or elemental mapping images of the sample constituting the first series of tilted images by some of the electron microscope images or elemental mapping images of the sample constituting the second series of tilted images so as to create a third series of tilted images.

In this image processor, the dependence of the elemental mapping images constituting the third series of tilted images on tilt angle can be reduced and so an accurate three-dimensional image can be obtained.

(13) In one feature of these image processors, the elemental mapping images of the sample may be obtained by irradiating the sample with an electron beam to induce X-rays and detecting the X-rays by an energy dispersive X-ray detector.

In these image processors, an accurate three-dimensional elemental distribution image can be obtained.

(14) An electron microscope associated with the present invention includes an image processor as herein described.

In this electron microscope, an accurate three-dimensional image can be obtained.

DESCRIPTION OF THE INVENTION

The preferred embodiments of the present invention are hereinafter described in detail with reference to the drawings. It is to be understood that the embodiments provided below do not unduly restrict the scope and content of the present invention delineated by the appended claims and that not all the configurations described below are essential constituent components of the invention.

1. IMAGE PROCESSOR AND ELECTRON MICROSCOPE

Figure 1:
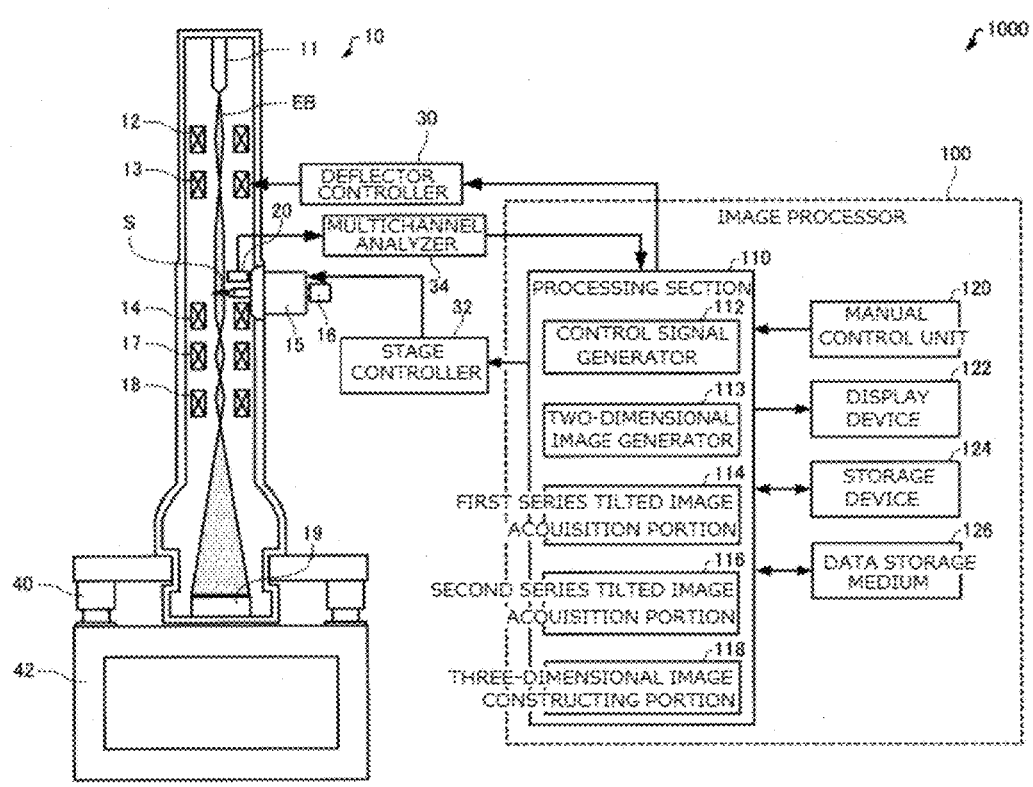
FIG. 1 is a schematic representation, partly in block form, of an electron microscope including an image processor associated with one embodiment of the present invention.

An electron microscope including an image processor associated with one embodiment of the present invention is first described by referring to FIG. 1, which schematically shows the configuration of the electron microscope, 1000, including the image processor, 100, associated with the present embodiment. In FIG. 1, the polepieces of an objective lens 14 are omitted from being shown for the sake of convenience.

The electron microscope 1000 includes a microscope body 10 and the image processor 100 as shown in FIG. 1.

For example, the microscope body 10 has the structure of a scanning transmission electron microscope (STEM). A scanning transmission electron microscope is an instrument for scanning an electron probe over a sample S, detecting electrons transmitted through the sample S, and obtaining an STEM image. The microscope body 10 is equipped with an energy dispersive X-ray spectrometer (also referred to as an EDS detector) 20.

The electron microscope body 10 includes an electron beam source 11, a condenser lens system 12, a scan deflector 13, the objective lens 14, a sample stage 15, a sample holder 16, an intermediate lens 17, a projector lens 18, a transmitted electron detector 19, the EDS detector 20, a deflector controller 30, a stage controller 32, and a multichannel analyzer (MCA) 34.

The electron beam source 11 produces an electron beam EB by accelerating electrons, which are emitted from a cathode, by means of an anode. For example, an electron gun can be used as the electron beam source 11. No restriction is placed on the electron gun used as the electron beam source 11. For example, a thermionic-emission electron gun, a thermal field-emission electron gun, a cold field emission electron gun, or other electron gun can be used.

The condenser lens system 12 is disposed behind (on the downstream side as viewed along the stream of the electron beam EB) the electron beam source 11. The electron beam EB produced by the electron beam source 11 is focused onto the sample S by the condenser lens system 12. The condenser lens system 12 may be configured including a plurality of lenses (not shown).

The scan deflector 13 is disposed behind the condenser lens system 12. The scan deflector 13 scans the electron beam EB (electron probe) over the sample S by deflecting the beam EB which, in turn, has been focused by both condenser lens system 12 and objective lens 14. The deflector 13 has deflection coils for deflecting the beam EB. The operation of the scan deflector 13 is controlled by the deflector controller 30. The controller 30 controls the operation of the scan deflector 13 on the basis of a scan signal generated by a control signal generator 112 (described later).

The objective lens 14 is located behind the scan coils of the scan deflector 13. The objective lens 14 is used to focus the electron beam EB onto the sample S.

The sample stage 15 holds the sample S. In the illustrated example, the sample stage 15 holds the sample S via the sample holder 16. The sample stage 15 can place the sample S in position by moving and stopping the sample holder 16. The sample stage 15 can move the sample S in a horizontal direction perpendicular to the direction of travel of the electron beam EB and in a vertical direction that is along the direction of travel of the beam EB.

Figure 2:
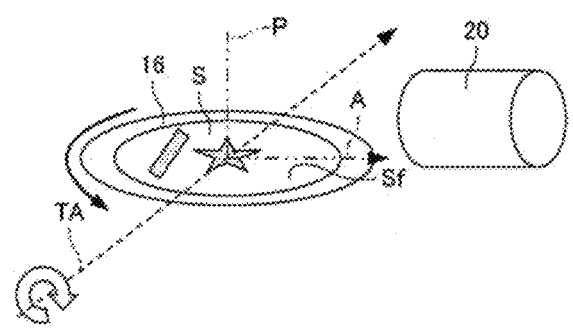
FIGS. 2 and 3 are diagrams illustrating the operation of a sample stage included in the microscope shown in FIG. 1.
Figure 3:
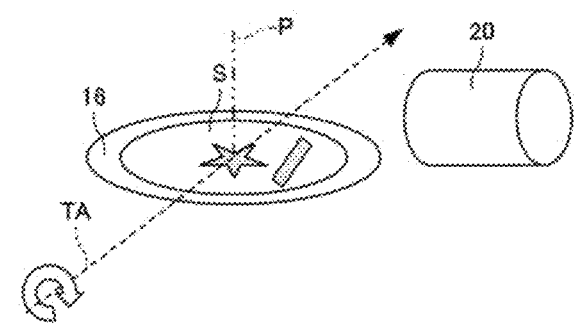

FIGS. 2 and 3 illustrate the operation of the sample stage 15. FIG. 3 shows a state in which the sample S has been rotated through 180 degrees about an axis P.

The sample stage 15 can tilt the sample S, for example, about a tilted axis TA perpendicular to the optical axis, for example, within a range of ±60 degrees.

As shown in FIGS. 2 and 3, the sample stage 15 can rotate the sample S about the axis P perpendicular to a surface Sf of the sample S, for example, through 180 degrees. For example, the sample surface Sf is a virtual plane representing a surface of the sample S on which the electron beam EB impinges when this surface is assumed to be planar. The sample stage 15 is controlled by the stage controller 32.

In the illustrated example, the sample stage 15 is a side entry stage for inserting the sample S from a side of the polepieces (not shown) of the objective lens 14. Alternatively, the sample stage 15 may be a top-loading stage for inserting the sample S from above the polepieces in an unillustrated manner.

The intermediate lens 17 is disposed behind the objective lens 14. The projector lens 18 is located behind the intermediate lens 17. The intermediate lens 17 and projector lens 18 cooperate to guide the electron beam EB transmitted through the sample S to the transmitted electron detector 19. For example, the intermediate lens 17 and projector lens 18 project and focus an image plane or back focal plane of the objective lens 14, where a diffraction pattern is formed, onto the electron detector 19.

The transmitted electron detector 19 is disposed behind the projector lens 18 and detects electrons transmitted through the sample S. An STEM image can be obtained by imaging the output signal from the transmitted electron detector 19 in synchronism with the scan signal.

The EDS detector 20 detects characteristic X-rays emanating from the sample S when it is irradiated with the electron beam EB. A silicon drift detector (SDD), a Si (Li) detector, or the like can be used as the EDS detector 20. Output pulses from the EDS detector 20 are sent to the multichannel analyzer 34.

The multichannel analyzer 34 is a pulse-height analyzer having a plurality of channels. The analyzer 34 counts the output pulses from the EDS detector 20 for each energy of X-rays, generates information about an EDS spectrum, and sends this information to a processing section 110 (see FIG. 1).

Figure 4:
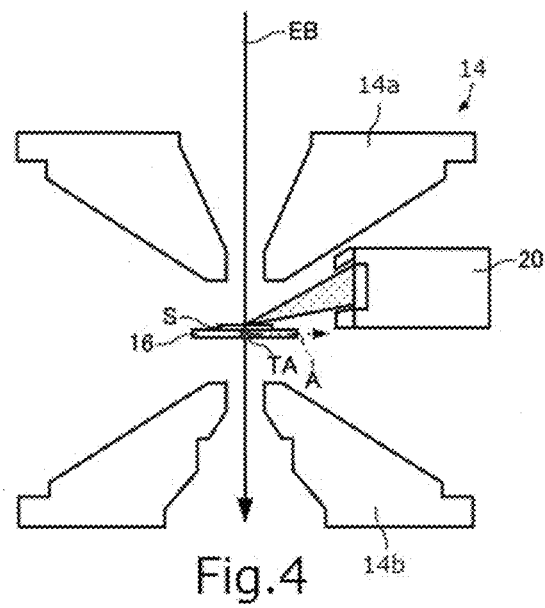
FIGS. 4 and 5 are schematic representations illustrating the positional relationship between an EDS detector and a sample.
Figure 5:
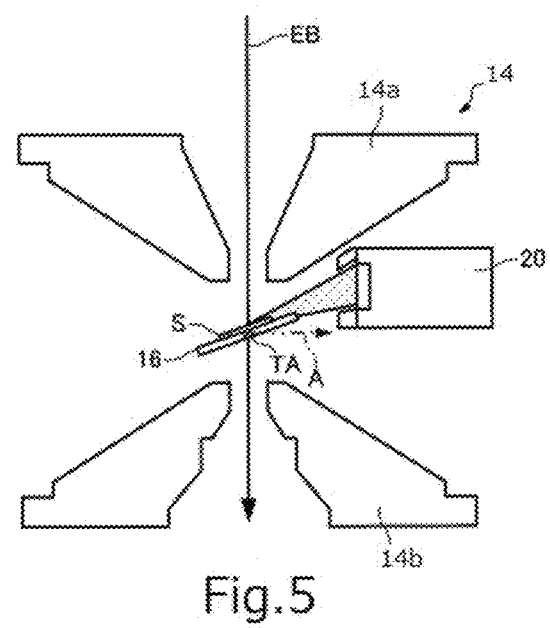

FIGS. 4 and 5 schematically show the positional relationship between the EDS detector 20 and the sample S in the electron microscope 1000. FIG. 4 shows a state in which the sample S is placed horizontally. FIG. 5 shows a state in which the sample S is at an angle.

As shown in FIGS. 4 and 5, the objective lens 14 has an upper polepiece 14a and a lower polepiece 14b and produces a magnetic field between the upper polepiece 14a and the lower polepiece 14b to focus the electron beam EB. The sample stage 15 places the sample S, which is held on the sample holder 16, for example, between the upper polepiece 14a and the lower polepiece 14b of the objective lens 14. The gap between the upper polepiece 14a and the lower polepiece 14b is so sized that even if the sample S is tilted at a large angle by the sample stage 15, no mechanical interference will occur.

As shown in FIGS. 4 and 5, the EDS detector 20 is located at a side of the objective lens 14. More specifically, the EDS detector 20 lies in a direction A that is perpendicular to the tilted axis TA and also to the optical axis (direction of travel of the electron beam EB), as viewed from the objective lens 14. Since the sample S is located between the upper polepiece 14a and the lower polepiece 14b of the objective lens 14, the EDS detector 20 is located beside the sample S, i.e., located in the direction A as viewed from the sample S. Since the EDS detector 20 is located at a side of the sample (objective lens 14), at a certain tilt angle, at least some of characteristic X-rays emanating from the sample S are cut off by the sample holder 16 and the sample S itself and not detected by the EDS detector 20 as shown in FIG. 5.

Referring back to FIG. 1, the electron microscope body 10 is installed on a pedestal 42 via vibration isolators 40.

The image processor 100 constructs a three-dimensional elemental distribution image of the sample S by EDS tomography. As shown in FIG. 1, the image processor 100 includes the processing section 110, a manual control unit 120, a display device 122, a storage device 124, and a data storage medium 126.

The manual control unit 120 obtains a manual control signal responsive to a user's manipulation or action and sends the signal to the processing section 110. The manual control unit 120 is made of buttons, keys, a touch panel display, a microphone, or the like.

The display device 122 displays images generated by the processing section 110. The function of the display device 122 can be implemented by an LCD, a CRT, or the like. The display device 122 displays a three-dimensional distribution image, for example, of the sample S generated by the processing section 110. Furthermore, the display device 122 can display elemental mapping images constituting first and second series of tilted images respectively obtained by a first series tilted image acquisition portion 114 and a second series tilted image acquisition portion 116 described later.

The storage device 124 acts as a working area for the processing section 110. The function of the storage device 124 is implemented by a RAM or the like. Computer programs, data, and related information permitting the processing section 110 to perform various control operations and computational operations are stored in the storage device 124. The storage device 124 is used also to temporarily store the results of computations performed by the processing section 110 in accordance with various programs.

The data storage medium 126 that is a computer-readable medium stores computer programs, data, and related information. The function of the storage medium 126 is implemented by an optical disc (such as a CD or a DVD), a magnetooptical disc (MO), a magnetic disc, hard disc, magnetic tape, memory (ROM), or the like. The processing section 110 performs various kinds of processing of the present embodiment on the basis of program and data stored in the data storage medium 126. Programs for causing a computer to operate as various portions of the processing section 110 can be stored in the storage medium 126.

The processing section 110 performs various kinds of control operations and computational operations in accordance with computer programs stored in the data storage medium 126. The processing section 110 operates as the control signal generator 112, a two-dimensional image generator 113, the first series tilted image acquisition portion 114, the second series tilted image acquisition portion 116, and a three-dimensional image constructing portion 118 described later by executing programs stored in the data storage medium 126. The functions of the processing section 110 can be implemented by hardware such as various processors (e.g., CPU and DSP) or ASIC (e.g., gate array) or by software. At least a part of the processing section 110 may be realized by hardware such as dedicated circuitry.

The control signal generator 112 generates various control signals and outputs them to the deflector controller 30, stage controller 32, and other devices. For example, the control signal generator 112 generates a scan signal and outputs it to the deflector controller 30. Furthermore, the control signal generator 112 generates a control signal for tilting the sample S in a plurality of angular increments and outputs the signal to the stage controller 32. In addition, the control signal generator 112 generates a control signal for rotating the sample S through a given angle such as 180 degrees about the axis P and outputs this signal to the stage controller 32.

The two-dimensional image generator 113 accepts the EDS spectrum information delivered from the multichannel analyzer 34 and generates an elemental mapping image (two-dimensional elemental distribution image) of the sample S. The two-dimensional image generator 113 obtains information about the X-ray intensities intrinsic to individual chemical elements on the basis of the EDS spectrum information and generates an elemental mapping image by synchronizing a brightness signal responsive to the intensities with the scan signal.

The first series tilted image acquisition portion 114 accepts the elemental mapping image information delivered from the two-dimensional image generator 113 and obtains an elemental mapping image. The first series tilted image acquisition portion 114 obtains a first series of tilted images by deriving elemental mapping images at different tilt angles which have been obtained by tilting the sample S in angular increments. For example, the first series tilted image acquisition portion 114 obtains the first series of tilted images by obtaining 25 elemental mapping images which are obtained when the sample S is tilted in 25 angular increments of 5 degrees from +60 degrees to −60 degrees.

The second series tilted image acquisition portion 116 obtains elemental mapping images after the sample S has been rotated through 180 degrees about the axis P when the sample S is in the same state as when the elemental mapping images constituting the first series of tilted images were obtained. Information about the latter elemental mapping images is output from the two-dimensional image generator 113.

Assuming that the elemental mapping images constituting the first series of tilted images are obtained under the state (i.e., the orientation) of the sample S shown in FIG. 2, the elemental mapping images constituting the second series of tilted images are obtained under the state of the sample S shown in FIG. 3.

The second series tilted image acquisition portion 116 obtains the second series of tilted images by obtaining elemental mapping images at different tilt angles by tilting the sample S, which has been rotated, in the angular increments. That is, the second series of tilted images is made up of a plurality of elemental mapping images obtained at different tilt angles. For example, the second series tilted image acquisition portion 116 obtains the second series of tilted images by tilting the sample S in 25 angular increments of 5 degrees from +60 degrees to −60 degrees so as to obtain 25 elemental mapping images. The elemental mapping images constituting the second series of tilted images are obtained, for example, under the same measuring conditions as for the elemental mapping images constituting the first series of tilted images. That is, the elemental mapping images constituting the first series of tilted images and the elemental mapping images constituting the second series of tilted images are identical, for example, in field of view for measurement and in dose of the electron beam EB. They are obtained using the same range of tilt angles and the same angular increment.

The three-dimensional image constructing portion 118 builds a three-dimensional image on the basis of the first and second series of tilted images. The 3D image constructing portion 118 rotates the elemental mapping images constituting the second series of tilted images to the same orientation as the elemental mapping images constituting the first series of tilted images. The 3D image constructing portion 118 replaces some of the elemental mapping images constituting the first series of tilted images by some of the elemental mapping images constituting the second series of tilted images so as to create a third series of tilted images.

For example, the 3D image constructing portion 118 creates the third series of tilted images by replacing elemental mapping images having lower levels of brightness (lower X-ray counts) out of the elemental mapping images constituting the first series of tilted images by the elemental mapping images constituting the second series of tilted images. For example, the 3D image constructing portion 118 measures the brightness levels of the elemental mapping images constituting the first series of tilted images and selects elemental mapping images of lower brightness levels to be replaced.

The three-dimensional image constructing portion 118 may subject the elemental mapping images lying in a predetermined angular range to replacement. This angular range of mapping images subject to replacement can be set by previously empirically or computationally finding an angular range in which the brightness levels of the elemental mapping images decrease because the EDS detector 20 is hidden in the shadow of the sample holder 16 or of the sample S itself.

Alternatively, a human operator may check the elemental mapping images constituting the first series of tilted images displayed on the display device 122 and select elemental mapping images subject to replacement.

Thus, the three-dimensional image constructing portion 118 replaces some of the first elemental mapping images constituting the first series of tilted images by some of the second elemental mapping images constituting the second series of tilted images, thus forming a third series of tilted images.

The three-dimensional image constructing portion 118 operates to construct a three-dimensional image by applying a computerized tomography (CT) method to plural elemental mapping images constituting the created third series of tilted images. Specifically, the 3D image constructing portion 118 reconstructs cross-sectional images from the elemental mapping images constituting the third series of tilted images and superimposes the obtained series of reconstructed cross-sectional images to construct a three-dimensional image (three-dimensional elemental distribution image).

2. METHOD OF CONSTRUCTING THREE-DIMENSIONAL IMAGE

Figure 6:
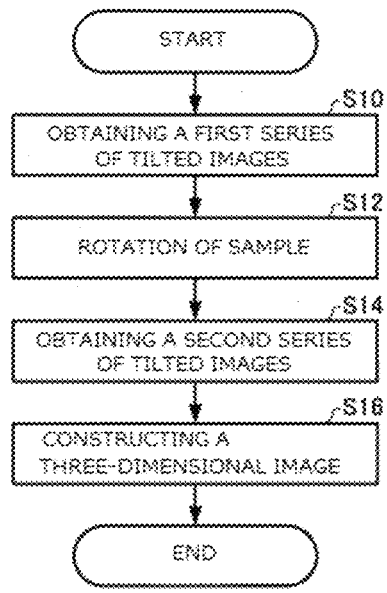
FIG. 6 is a flowchart illustrating one example of a method associated with one embodiment of the present invention to construct a three-dimensional image.

A method of constructing a three-dimensional image of the sample S using the electron microscope 1000 including the image processor 100 associated with the present embodiment is next described by referring to FIG. 6, which is a flowchart illustrating one example of the method of constructing a three-dimensional image in accordance with the present embodiment.

First, a first series of tilted image is obtained (step S10).

In particular, the control signal generator 112 generates a control signal for tilting the sample S in angular increments and outputs the signal to the stage controller 32. The stage controller 32 controls the sample stage 15 in response to the signal to tilt the sample S in the angular increments. Furthermore, the control signal generator 112 outputs a scan signal for scanning the electron beam EB over the sample S to the deflector controller 30 at each tilt angle. Consequently, EDS mapping can be performed at each tilt angle. The two-dimensional image generator 113 generates elemental mapping images at different tilt angles.

The first series tilted image acquisition portion 114 obtains the first series of tilted images by obtaining those elemental mapping images at different tilt angles which have been produced by the two-dimensional image generator 113.

Then, the sample S is rotated through 180 degrees about the axis P perpendicular to the sample surface Sf (step S12).

In particular, the control signal generator 112 generates a control signal for rotating the sample S through 180 degrees about the axis P and outputs the signal to the stage controller 32. The stage controller 32 controls the sample stage 15 in response to the control signal to rotate the sample S through 180 degrees about the axis P.

The present step may also be carried out, for example, by removing the sample S from the sample holder 16 by a human operator, then rotating the sample S through 180 degrees, and reinstalling the sample on the sample holder 16. That is, the present step may be manually conducted by the operator.

Then, the second series of tilted images is obtained (step S14).

This step S14 can be performed similarly to step S10 except that this step S14 is performed after the sample S is rotated through 180 degrees about the axis P and that the second series tilted image acquisition portion 116 obtains elemental mapping images at different tilt angles. Furthermore, step S14 is carried out in the same measuring conditions as for step S10. That is, steps S14 and S10 are identical, for example, in range of tilt angles and in angular increment. In addition, steps S14 and S10 are identical, for example, in measuring range and in dose of the electron beam EB.

In step S14, the second series tilted image acquisition portion 116 obtains elemental mapping images of the sample S, which has been rotated through 180 degrees about the axis P, at different tilt angles and derives a second series of tilted images.

Then, a three-dimensional image is constructed (step S16).

The three-dimensional image constructing portion 118 constructs a three-dimensional image on the basis of the first and second series of tilted images. In particular, the 3D image constructing portion 118 creates a third series of tilted images by replacing elemental mapping images which are included in the elemental mapping images constituting the first series of tilted images and which are lower in brightness level than other elemental mapping images by the elemental mapping images constituting the second series of tilted images. The 3D image constructing portion 118 operates to apply computerized tomography to the elemental mapping images constituting the third series of tilted images for generating a three-dimensional image and to display the generated three-dimensional image on the display device 122. Because of the processing steps described so far, a three-dimensional image (three-dimensional elemental distribution image) of the sample S can be built.

The three-dimensional image constructing method and image processor 100 associated with the present embodiment have the following features. The three-dimensional image constructing method associated with the present embodiment comprises the step S10 of obtaining the first series of tilted images which are constituted by elemental mapping images at different tilt angles and which have been obtained by tilting the sample S in a plurality of angular increments, the step S14 of obtaining the second series of tilted images which are constituted by elemental mapping images at different tilt angles and which have been obtained by rotating the sample S about the axis P when the sample is in the same state as when the first series of tilted images was obtained and then tilting the sample S in a plurality of angular increments, and the step S16 of constructing a three-dimensional image on the basis of the first and second series of tilted images.

If the sample S is tilted in increments, the EDS detector 20 may become hidden in the shadow of any one of the sample holder 16, mesh holding the sample S, and the sample S itself at a certain tilt angle, and the generated characteristic X-rays are cut off and the X-ray intensity decreases, reducing the brightness levels of the elemental mapping images. In the three-dimensional image constructing method associated with the present embodiment, a three-dimensional image can be built by replacing elemental mapping images which are included in the elemental mapping images constituting the first series of tilted images and which have decreased in brightness level because the characteristic X-rays are cut off as described above by the elemental mapping images constituting the corresponding second series of tilted images. Consequently, the dependence of the elemental mapping images constituting the series of tilted images for constructing a three-dimensional image on tilt angle (i.e., variation in brightness level among tilt angles) can be reduced. Hence, an accurate three-dimensional image can be obtained.

In the embodiment associated with the present embodiment to construct a three-dimensional image, the step S12 of rotating the sample S through 180 degrees about the axis P is carried out after the step S10 of obtaining the first series of tilted images and prior to the step S14 of obtaining the second series of tilted images. Consequently, the elemental mapping images constituting the second series of tilted images can be made to correspond to the elemental mapping images constituting the first series of tilted images by rotating the elemental mapping images constituting the second series of tilted images through 180 degrees. Thus, the elemental mapping images constituting the first series of tilted images can be easily replaced by the elemental mapping images constituting the second series of tilted images.

In the method associated with the present embodiment to construct a three-dimensional image, a three-dimensional image is fabricated by rotating the elemental mapping images of the sample S constituting the second series of tilted images to the same orientation as the elemental mapping images of the sample S constituting the first series of tilted images and replacing some of the elemental mapping images constituting the first series of tilted images by some of the elemental mapping images constituting the second series of tilted images so as to create a third series of tilted images. Consequently, the dependence of the elemental mapping images constituting the series of tilted images for constructing a three-dimensional image on tilt angle can be reduced and thus an accurate three-dimensional image can be obtained.

In the image processor 100, the three-dimensional image constructing portion 118 constructs a three-dimensional image on the basis of the first and second series of tilted images and so the dependence of the elemental mapping images constituting the series of tilted images for constructing a three-dimensional image on tilt angle can be reduced as described previously. As a result, an accurate three-dimensional image can be derived.

The electron microscope 1000 includes the image processor 100 and, therefore, an accurate three-dimensional image can be obtained.

3. EXAMPLES

The present embodiment is described in further detail below by taking its examples. However, the present invention is not restricted thereby.
(1) Sample
A coated film sectioned into ultrathin slices by a microtome was used as a sample.
(2) Acquisition of Series of Tilted Images
First, the sample was tilted in a plurality of angular increments to perform EDS mapping at each tilt angle. An elemental mapping image at each tilt angle was acquired, thus obtaining a first series of tilted images. Then, the sample was rotated through 180 degrees relative to a line perpendicular to the sample surface. In particular, a sample was rotated through 180 degrees about a vertical axis while kept placed horizontally, i.e., at a tilt angle of 0 degree. Then, the rotated sample was tilted in angular increments to perform EDS mapping at each tilt angle. Thus, an elemental mapping image was acquired at each tilt angle. In this way, a second series of tilted images was obtained.

The measurements were performed using JEM-2100F (a transmission electron microscope manufactured by JEOL Ltd.). A solid state detector (SDD) of 60 mm² was used as an EDS detector.

Figure 7:
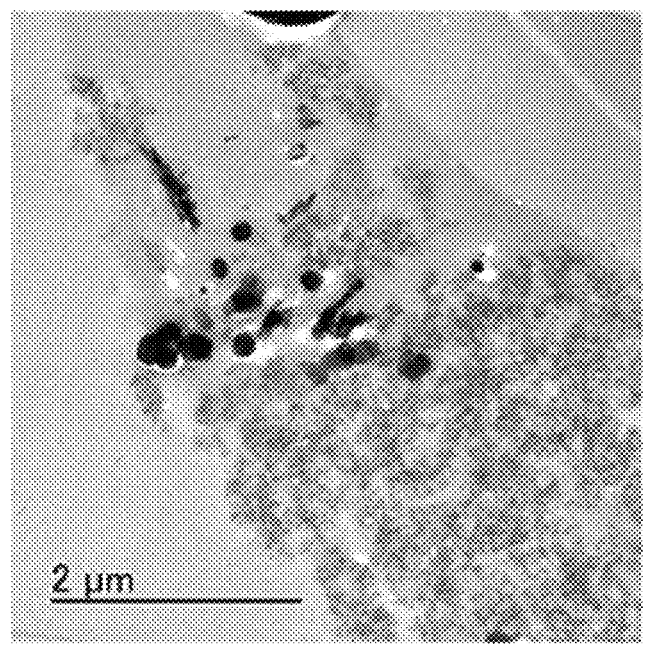
FIG. 7 is a TEM image of a sample consisting of a coated film.
Figure 8:
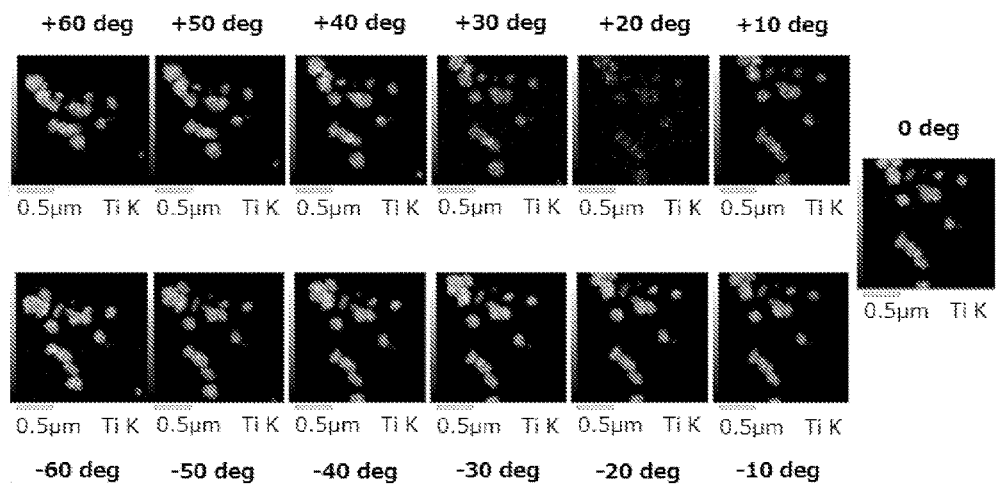
FIG. 8 shows some of elemental mapping images that constitute a first series of tilted images.
Figure 9:
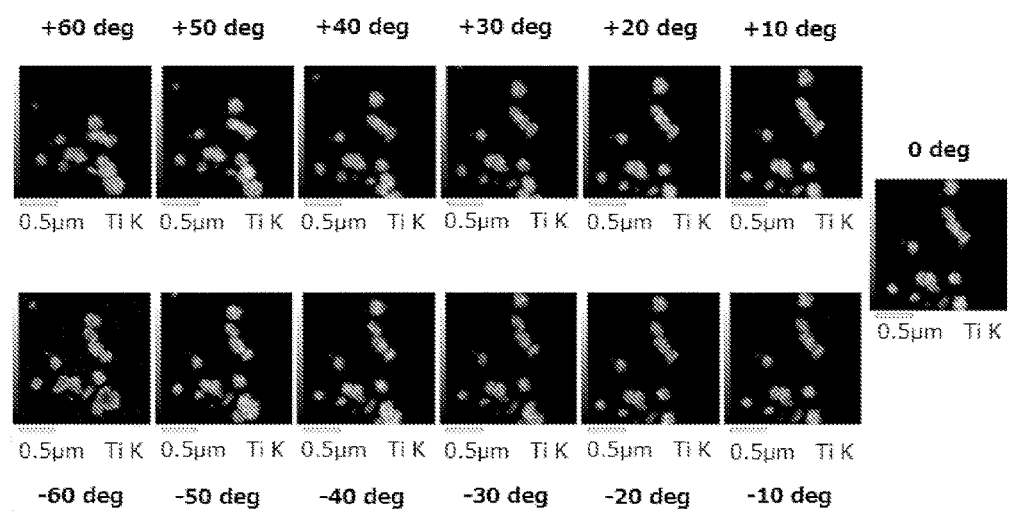
FIG. 9 shows some of elemental mapping images that constitute a second series of tilted images.

The measuring conditions under which the first series of tilted images was obtained and the measuring conditions under which the second series of tilted images was obtained were made identical. In particular, the angular increment was 5 degrees. The angular range of tilt angles was from −60 degrees to +60 degrees. That is, each of the first and second series of tilted images is made up of 25 elemental mapping images at different tilt angles. The size of each elemental mapping image was 256×256 pixels.
(3) Results of Measurements
FIG. 7 is a transmission electron microscope image of a sample made of a coated film. FIG. 8 shows some of elemental mapping images of Ti Kα line constituting the first series of tilted images. FIG. 9 shows some of elemental mapping images of Ti Kα line constituting the second series of tilted images.
(4) Construction of Three-Dimensional Image
First, a relationship between the tilt angle at which each elemental mapping image constituting the first series of tilted images was obtained and the brightness level was found.

Figure 10:
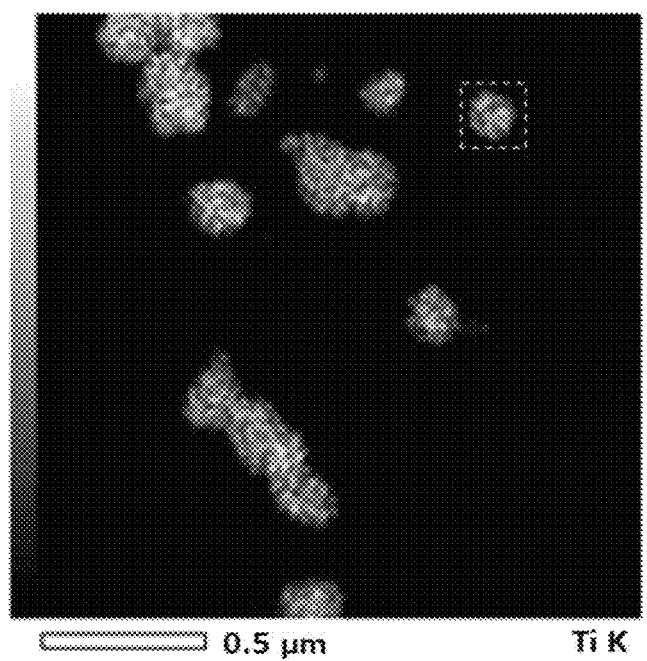
FIG. 10 is an elemental mapping image formed at a tilt angle of 0 degree and constituting the first series of tilted images.

FIG. 10 is an elemental mapping image at a tilt angle of 0° constituting the first series of tilted images. One particle surrounded by the dotted square in FIG. 10 was noticed. The tilt angle was plotted on the horizontal axis, while X-ray count of Ti Kα line produced from this particle was plotted on the vertical axis. The results are shown in FIG. 11.

Figure 11:
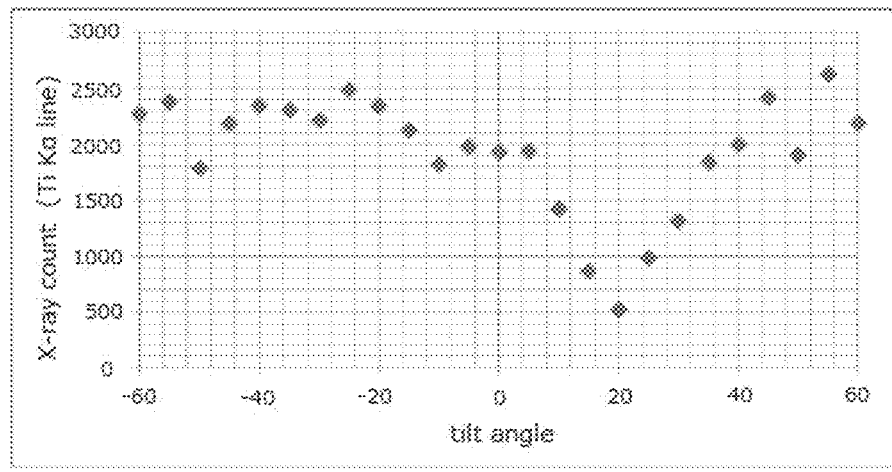
FIG. 11 is a graph showing a relationship between X-ray counts for the first series of tilted images and tilt angle.

It is seen from FIG. 11 that the X-ray count dropped extremely in the neighborhood of a tilt angle+20° (+5° to +35°). It is considered that characteristic X-rays emanating from the sample are cut off by the sample holder and so on. From the results shown in FIG. 11, the angular range of tilt angles at which the elemental mapping images subject to replacement were obtained has been set to be from +5° to +60° in which the X-ray counts were relatively low.

Then, the elemental mapping images obtained at tilt angles of +5° to +60° and constituting the first series of tilted images were replaced by the elemental mapping images obtained in the corresponding range of tilt angles and constituting the second series of tilted images. At this time, the elemental mapping images constituting the second series of tilted images which were replacements were rotated through 180 degrees to the same orientation as the elemental mapping images constituting the first series of tilted images. In this way, a third series of tilted images was created.

Figure 12:
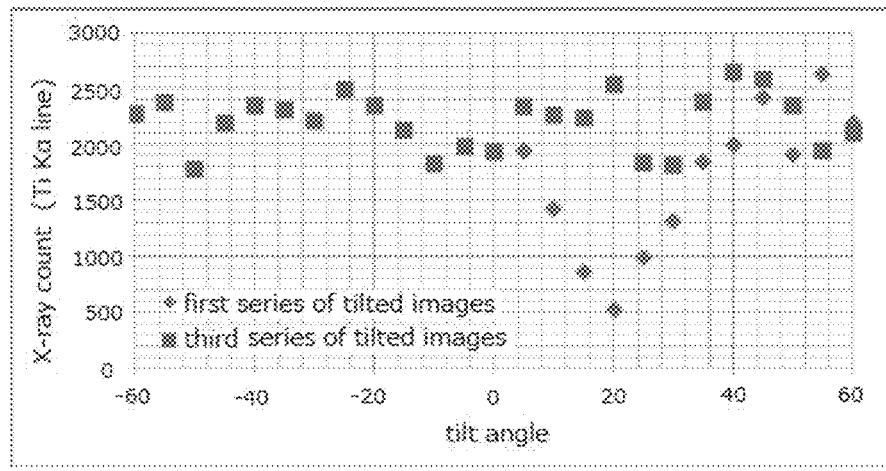
FIG. 12 is a graph showing a relationship between X-ray counts for the third series of tilted images and tilt angle.

FIG. 12 is a graph showing a relationship between X-ray count and tilt angle in the third series of tilted images. The graph shown in FIG. 12 was generated in the same way as the graph shown in FIG. 11. That is, one particle surrounded by the dotted square shown in FIG. 10 was noticed. Tilt angle was plotted on the horizontal axis, while X-ray count for Ti Kα line produced from this particle was plotted on the vertical axis.

It is observed from the graph of FIG. 12 that the X-ray counts in the neighborhood of the tilt angle of +20° did not drop. That is, it can be said that the third series of tilted images has less dependence on tilt angle than the first series of tilted images.

A three-dimensional image was then constructed by computerized tomography from the 25 elemental mapping images of Ti constituting the third series of tilted images. Similarly, three-dimensional images were constructed from elemental mapping images of Fe, Si, and O, respectively.

Figure 13:
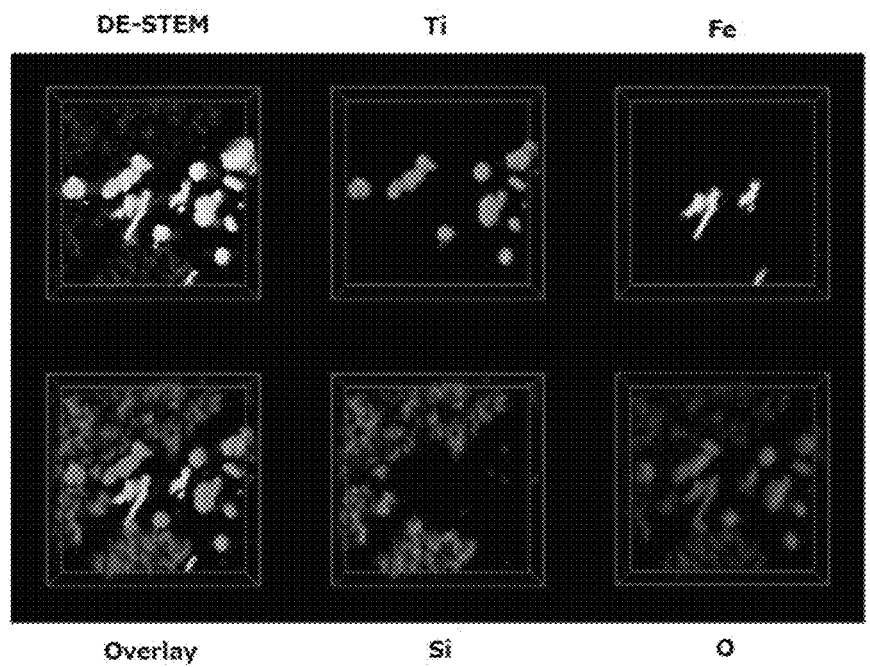
FIG. 13 shows constructed three-dimensional images.

FIG. 13 shows the constructed three-dimensional images. Shown in FIG. 13 are a dark field (DF) STEM image, a three-dimensional elemental distribution image of Ti, a three-dimensional elemental distribution image of Fe, a three-dimensional elemental distribution image of Si, a three-dimensional elemental distribution image of O, and a superimposition of the three-dimensional distribution images of Ti, Fe, Si, and O.

As shown in FIG. 13, the distributions of the elements are observed clearly and thus accurate three-dimensional elemental distribution images have been obtained.

4. MODIFICATIONS

It is to be understood that the present invention is not restricted to the above-described embodiment but rather can be implemented in various forms without departing from the gist of the present invention.
(1) First Modification
A first modification is first described. Only differences with the above-described examples of image processor 100 and electron microscope 1000 are described. A description of similarities is omitted.

In the image processor 100 described above, the second series tilted image acquisition portion 116 obtains a second series of tilted images which constitute elemental mapping images at different tilt angles and which have been derived by tilting the sample S in plural angular increments after the sample S has been rotated about the axis P through 180 degrees.

In contrast, in the present modification, the second series tilted image acquisition portion 116 obtains a second series of tilted images which consist of elemental mapping images at different tilt angles and which have been obtained by tilting the sample S in plural angular increments after the sample S is turned upside down when the sample S is in the same state as when the elemental mapping images constituting the first series of tilted images were obtained.

Figure 14:
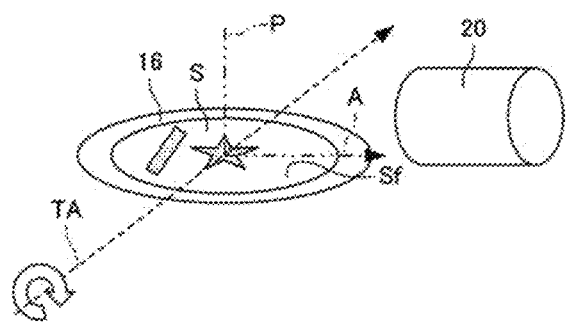
FIGS. 14 and 15 are diagrams illustrating the operation of the sample stage.
Figure 15:
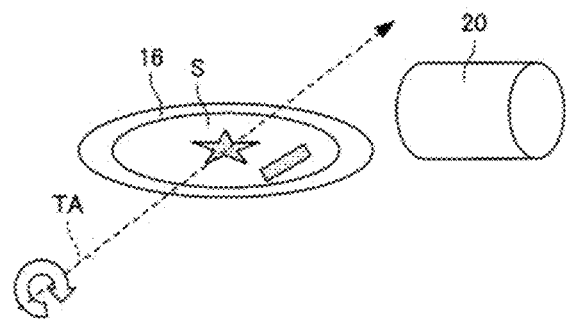

The sample stage 15 can turn the sample S upside down. FIGS. 14 and 15 illustrate the operation of the sample stage 15. The sample stage 15 can turn the sample S upside down as shown in FIG. 15, for example, when the stage 15 is in the state shown in FIG. 14 by rotating the sample S about the tilted axis TA through 180 degrees.

Figure 16:
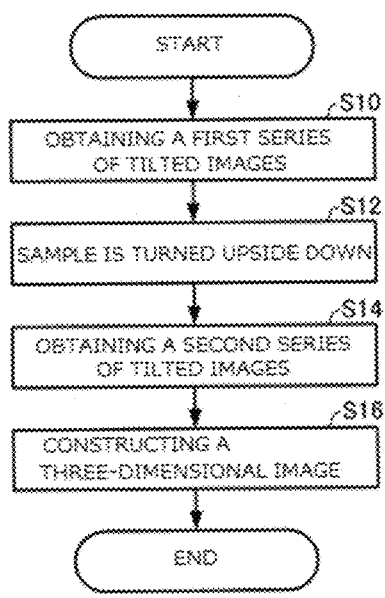
FIG. 16 is a flowchart illustrating one example of method of associated with a first modification to fabricate a three-dimensional image.

A method associated with the present modification to construct a three-dimensional image is next described by referring to FIG. 16, which is a flowchart illustrating one example of the method of constructing a three-dimensional image in accordance with the first modification.

First, a first series of tilted images is obtained (step S10). This step S10 is the same as the step S10 already described in connection with FIG. 6 and so a description thereof is omitted.

Then, the sample S is turned upside down (step S13).

In particular, the control signal generator 112 generates a control signal for turning the sample S upside down (i.e., rotating the sample S about the tilted axis TA through 180 degrees) and outputs the signal to the stage controller 32. The stage controller 32 controls the sample stage 15 on the basis of this control signal and turns the sample S upside down.

Alternatively, the present step may be carried out by turning the sample S upside down and reinstalling the sample S on the holder 16 after the operator removes the sample S from the sample holder 16.

Then, a second series of tilted image is obtained (step S14). This step S14 is similar to the step S14 illustrated in FIG. 6 except that this step S14 of FIG. 16 is performed after the sample S has been reversed and so a description of the step S14 of FIG. 16 is omitted.

A three-dimensional image is then constructed (step S16). This step S16 is similar to the step S16 illustrated in FIG. 6 except that the three-dimensional image constructing portion 118 reverses the elemental mapping images constituting the second series of tilted images to the same orientation as the elemental mapping images constituting the first series of tilted images and so a description of this step S16 of FIG. 16 is omitted.

Because of the processing steps described so far, a three-dimensional elemental distribution image of the sample S can be fabricated.

The three-dimensional image constructing method and image processor associated with the present modification can yield advantageous effects similar to those produced by the above-described three-dimensional image constructing method and image processor 100 associated with the present embodiment.

(2) Second Modification

A second modification is next described. The above-described electron microscope 1000 is equipped with the EDS detector 20 as shown in FIG. 1. Alternatively, the microscope may be equipped with other detector. For example, the electron microscope 1000 may be equipped with a secondary electron detector instead of the EDS detector 20.

The secondary electron detector is disposed, for example, in a position similar to that of the EDS detector 20. Therefore, where a secondary electron detector is used, there is the problem that secondary electrons emanating from the sample S are cut off by the sample holder 16 and the sample S itself at certain angles in the same way as for the EDS detector 20. At this time, the image processor 100 performs processing similar to the processing in the above-described embodiment to construct a three-dimensional image from secondary electron images which are examples of electron microscope images. Consequently, an accurate three-dimensional image can be fabricated from secondary electron images.

Note that the above-described embodiment and modifications are merely exemplary and that the present invention is not restricted thereto. For example, the embodiment and modifications can be combined appropriately.

The present invention embraces configurations (e.g., configurations identical in function, method, and results or identical in purpose and advantageous effects) which are substantially identical to the configurations described in the above embodiment. Furthermore, the invention embraces configurations which are similar to the configurations described in the above embodiment except that their non-essential portions have been replaced. Additionally, the invention embraces configurations which are identical in advantageous effects to, or which can achieve the same object as, the configurations described in the above embodiment. Further, the invention embraces configurations which are similar to the configurations described in the above embodiment except that a well-known technique is added.

Having thus described my invention with the detail and particularity required by the Patent Laws, what is desired protected by Letters Patent is set forth in the following claims.

The invention claimed is:

1. A method of constructing a three-dimensional image, comprising the steps of:
    obtaining a first series of tilted images which are constituted by electron microscope images or elemental mapping images of a sample at different tilt angles and which have been obtained by tilting the sample in a plurality of angular increments;
    rotating the sample through 180 degrees about an axis perpendicular to the surface of the sample after the step of obtaining the first series of tilted images;
    obtaining a second series of corresponding tilted images which are constituted by electron microscope images or elemental mapping images of the sample at different tilt angles; and
    constructing the three-dimensional image on the basis of the first and second series of tilted images wherein, during the step of constructing the three-dimensional image, said second series of tilted images is rotated to the same orientation as said first series of tilted images and some of the electron microscope images or elemental mapping images of the sample constituting the first series of tilted images are replaced by some of the electron microscope images or elemental mapping images of the sample constituting the second series of tilted images so as to create a third series of tilted images for constructing the three-dimensional image.

2. The method of constructing a three-dimensional image as set forth in claim 1, wherein said elemental mapping images of the sample are obtained by irradiating the sample with an electron beam to induce X-rays and detecting the X-rays by an energy dispersive X-ray detector.

3. A method of constructing a three-dimensional image, comprising the steps of:

obtaining a first series of tilted images which are constituted by electron microscope images or elemental mapping images of a sample at different tilt angles and which have been obtained by tilting the sample in a plurality of angular increments;

turning the sample upside down after the step of obtaining said first series of tilted images and prior to the step of obtaining said second series of tilted images;

obtaining a second series of corresponding tilted images which are constituted by electron microscope images or elemental mapping images of the sample at different tilt angles; and constructing the three-dimensional image on the basis of the first and second series of tilted images, wherein said three-dimensional image is constructed by reversing said second series of tilted images to the same orientation as said first series of tilted images and replacing some of the electron microscope images or elemental mapping images of the sample constituting the first series of tilted images by some of the electron microscope images or elemental mapping images of the sample constituting the second series of tilted images so as to create a third series of tilted images for constructing the three-dimensional image.

4. An image processor comprising:

a first series tilted image acquisition portion for obtaining a first series of tilted images which are constituted by electron microscope images or elemental mapping images of a sample at different tilt angles and which have been obtained by tilting the sample in a plurality of angular increments;

means for rotating the sample about an axis perpendicular to the surface of the sample through 180 degrees when the sample is in the same state as when said first series of tilted images was obtained;

a second series tilted image acquisition portion for obtaining a second series of corresponding tilted images which are constituted by electron microscope images or elemental mapping images of the sample at different tilt angles; and a three-dimensional image constructing portion for constructing a three-dimensional image on the basis of the first and second series of tilted images, wherein said three-dimensional image constructing portion constructs said three-dimensional image by rotating said second series of tilted images to the same orientation as said first series of tilted images and replacing some of the electron microscope images or elemental mapping images of the sample constituting the first series of tilted images by some of the electron microscope images or elemental mapping images of the sample constituting said second series of tilted images so as to create a third series of tilted images.

5. The image processor as set forth in claim 4, wherein said elemental mapping images of the sample are obtained by irradiating the sample with an electron beam to induce X-rays and detecting the X-rays by an energy dispersive X-ray detector.

6. An electron microscope including an image processor as set forth in claim 4.

7. An image processor comprising:

a first series tilted image acquisition portion for obtaining a first series of tilted images which are constituted by electron microscope images or elemental mapping images of a sample at different tilt angles and which have been obtained by tilting the sample in a plurality of angular increments;

a second series tilted image acquisition portion for obtaining a second series of corresponding tilted images which are constituted by electron microscope images or elemental mapping images of the sample at different tilt angles and which have been obtained by turning the sample upside down when the sample is in the same state as when the first series of tilted images was obtained and then tilting the sample in a plurality of angular increments; and a three-dimensional image constructing portion for constructing a three-dimensional image on the basis of the first and second series of tilted images, wherein said three-dimensional image constructing portion constructs said three-dimensional image by reversing said second series of tilted images to the same orientation as said first series of tilted images and replacing some of the electron microscope images or elemental mapping images of the sample constituting the first series of tilted images by some of the electron microscope images or elemental mapping images of the sample constituting the second series of tilted images so as to create a third series of tilted images.

\* \* \* \* \*